(12) United States Patent
Lai et al.

(10) Patent No.: US 10,634,664 B2
(45) Date of Patent: Apr. 28, 2020

(54) BLOOD-GLUCOSE METER INTEGRATED WITH BIOLOGICAL TEST-PIECE TANK

(71) Applicant: OK BIOTECH CO. LTD., Hsinchu (TW)

(72) Inventors: Chia-Te Lai, Hsinchu (TW); An-Yuan Lee, Hsinchu (TW)

(73) Assignee: OK BIOTECH CO. LTD., Hsinchu (TW)

( * ) Notice: Subject to any disclaimer, the term of this patent is extended or adjusted under 35 U.S.C. 154(b) by 210 days.

(21) Appl. No.: 15/802,509

(22) Filed: Nov. 3, 2017

(65) Prior Publication Data
US 2019/0011431 A1 Jan. 10, 2019

(30) Foreign Application Priority Data
Jul. 7, 2017 (TW) .............................. 106122921 A

(51) Int. Cl.
| | |
|---|---|
| *G01N 33/50* | (2006.01) |
| *G01N 33/487* | (2006.01) |
| *A61B 5/145* | (2006.01) |
| *A61B 5/157* | (2006.01) |
| *H01B 7/00* | (2006.01) |
| *C12Q 1/00* | (2006.01) |

(52) U.S. Cl.
CPC .......... *G01N 33/50* (2013.01); *A61B 5/14532* (2013.01); *A61B 5/157* (2013.01); *G01N 33/4875* (2013.01); *H01B 7/009* (2013.01); *A61B 2562/0295* (2013.01); *C12Q 1/006* (2013.01)

(58) Field of Classification Search
CPC .. B01L 9/52; B01L 99/00; B01L 3/508; B01L 2300/0832; B01L 2300/0858; B01L 2300/0609; B01L 2200/022; B01L 2300/028; B01L 2300/0825; B01L 2300/0851; B01L 2300/043; B01L 2200/025; A61B 50/30; G01N 33/48778
See application file for complete search history.

(56) References Cited

U.S. PATENT DOCUMENTS

| | | | | |
|---|---|---|---|---|
| 2003/0133847 | A1* | 7/2003 | Hagen ............. | G01N 33/48757 422/430 |
| 2008/0118400 | A1* | 5/2008 | Neel ................ | G01N 33/48757 422/68.1 |
| 2010/0140116 | A1* | 6/2010 | Stiene ............... | B65D 81/266 206/204 |
| 2016/0157583 | A1* | 6/2016 | Winter .............. | A45D 34/00 215/227 |

\* cited by examiner

*Primary Examiner* — Matthew D Krcha
*Assistant Examiner* — Curtis A Thompson
(74) *Attorney, Agent, or Firm* — WPAT, PC

(57) ABSTRACT

A blood-glucose meter integrated with a biological test-piece tank includes a biological test-piece tank and a blood-glucose meter. The biological test-piece tank has internally a chamber for providing an accommodation room to store a plurality of biological test pieces, a tank opening located at a top thereof to pair a cover so as to form a sealed structure, and a tank bottom located by opposing to the cover. The blood-glucose meter, connected with the tank bottom, has an inserting hole for receiving a biological test piece that carries thereon a biological specimen to be examined for obtaining a corresponding blood-glucose value.

4 Claims, 4 Drawing Sheets

BLOOD-GLUCOSE METER INTEGRATED WITH BIOLOGICAL TEST-PIECE TANK

CROSS REFERENCE TO RELATED APPLICATION

This application claims the benefit of Taiwan Patent Application Serial No. 106122921, filed Jul. 7, 2017, the subject matter of which is incorporated herein by reference.

BACKGROUND OF THE INVENTION

(1) Field of the Invention

The invention relates to a blood-glucose meter integrated with a biological test-piece tank, and more particularly to a small-sized blood-glucose meter that integrates a biological test-piece tank so as to attain better preservation performance.

(2) Description of the Prior Art

Persons with diabetes need to detect their own blood-glucose concentrations frequently. Through the detections, levels of the blood-glucose concentrations can be acquired immediately, so that a comprehensive diet plan for controlling the blood-glucose concentration can be carried out. In testing the blood-glucose concentration, a biological test piece in a biological test-piece tank is inserted into a blood-glucose meter, and then a blood specimen on the biological test piece is analyzed by the blood-glucose meter to process various testing of the blood glucose. In the aforesaid testing, it is notorious that a biological test-piece tank shall be prepared in advance before a testing upon the blood-glucose meter can be taken. After the testing, it is also another notorious task to store the biological test-piece tank. The inventory of the biological test-piece tank and the blood-glucose meter is important; not only for the storage purpose, but also for the convenience of next usage. If such a storing job is not fairly done, it is quite possible that the blood-glucose meter and the biological test-piece tank cannot be found together or at the same time. Thus, a delay in testing is definitely possible.

Further, the biological test piece is opt to be affected with damp. It is obvious that a moisturized test piece cannot even help a well-calibrated biological test instrument to perform an accurate test. Thus, a biological test-piece tank shall be applied to keep the biological test pieces away from moisture. Currently, various types of the biological test-piece tanks can be seen already in the marketplace for preventing the biological test pieces from moistures. One type thereof is to apply an air-tight structure, another thereof is to vacuum the biological test-piece tank, and one more type thereof to add a dehydrator into the biological test-piece tank. Definitely, all the aforesaid types of the biological test-piece tanks have moisture-proof capability to some extent.

Hence, in order to obtain a goal of storing the biological test-piece tank and the blood-glucose meter together, and to achieve a preservation room for dry-keeping the biological test pieces in the biological test-piece tank, the effort to provide an improvement for meeting the aforesaid requirements is definitely welcome to the art.

SUMMARY OF THE INVENTION

Accordingly, it is an object of the present invention to provide a blood-glucose meter integrated with a biological test-piece tank that a small-sized blood-glucose meter and a biological test-piece tank are engaged structurally, such that the aforesaid problem in difficultly locating the blood-glucose meter and the biological test-piece tank at the same time would be resolved for good. Thus, preservation of the biological test pieces would become easy through the application of the blood-glucose meter integrated with the biological test-piece tank in accordance with the present invention.

It is another object of the present invention to provide a blood-glucose meter integrated with a biological test-piece tank that the structural engagement of the blood-glucose meter and the biological test-piece tank would render the combination to have a smaller volume, so that the total spatial occupation for storage would be substantially reduced, and thus the target of easy storage can be obtained.

It is a further object of the present invention to provide a blood-glucose meter integrated with a biological test-piece tank that, in usage, the blood-glucose meter can be optionally separated from the biological test-piece tank. Namely, the application of the blood-glucose meter of the present invention can be absolutely dependent on practical requirements, so that convenience of testing via the blood-glucose meter won't be reduced by integrating the additional biological test-piece tank.

In the present invention, the blood-glucose meter integrated with a biological test-piece tank includes a biological test-piece tank and a blood-glucose meter. The biological test-piece tank has internally a chamber for providing an accommodation room to store a plurality of biological test pieces, a tank opening located at a top thereof to pair a cover so as to form a sealed structure, and a tank bottom located by opposing to the cover. The blood-glucose meter, connected with the tank bottom, has an inserting hole for receiving a biological test piece that carries thereon a biological specimen to be examined for obtaining a corresponding blood-glucose value.

Preferably, an engagement means between the blood-glucose meter and the biological test-piece tank is a screw pair, the screw pair having external threads located exteriorly at the tank opening and corresponding internal threads located interiorly at the blood-glucose meter.

Preferably, an engagement means between the blood-glucose meter and the biological test-piece tank is a notch pair, the notch pair having a bulge ring located exteriorly at the tank bottom and a corresponding internal groove located interiorly at the blood-glucose meter.

Preferably, an engagement area of the blood-glucose meter and the biological test-piece tank is furnished with a C-shape internal-tooth ring for connecting the blood-glucose meter and the biological test-piece tank.

Preferably, the blood-glucose meter further includes a display unit for displaying the blood-glucose value of the specimen.

Preferably, the display unit is an LCD.

Preferably, the blood-glucose meter further includes a setup button for setting up related parameters.

All these objects are achieved by the blood-glucose meter integrated with a biological test-piece tank described below.

BRIEF DESCRIPTION OF THE DRAWINGS

The present invention will now be specified with reference to its preferred embodiment illustrated in the drawings, in which.

DESCRIPTION OF THE PREFERRED EMBODIMENT

The invention disclosed herein is directed to a blood-glucose meter integrated with a biological test-piece tank. In the following description, numerous details are set forth in order to provide a thorough understanding of the present invention. It will be appreciated by one skilled in the art that variations of these specific details are possible while still achieving the results of the present invention. In other instance, well-known components are not described in detail in order not to unnecessarily obscure the present invention.

Figure 1:
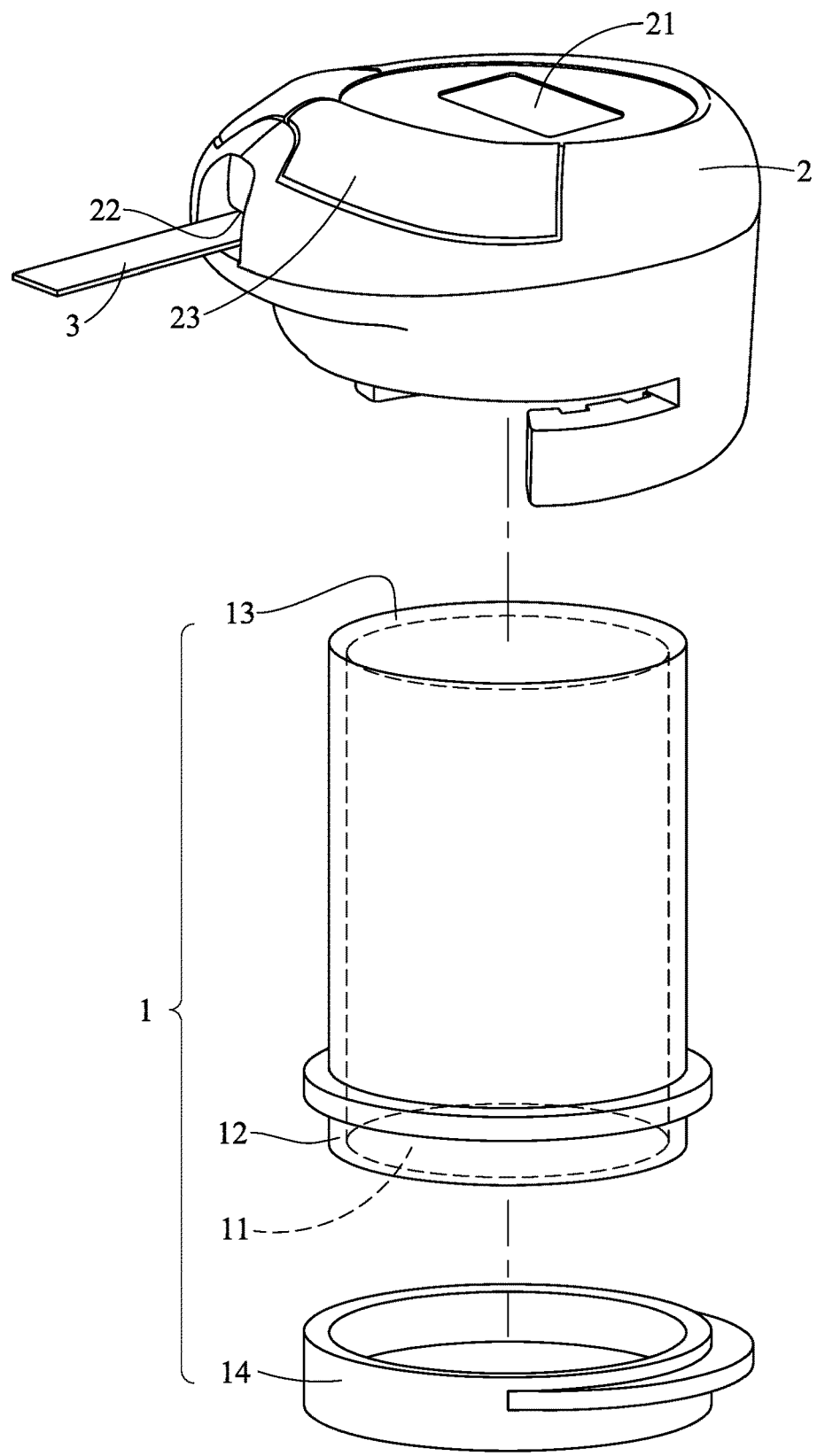
FIG. 1 is a largely exploded view of the blood-glucose meter integrated with a biological test-piece tank in accordance with the present invention.

Referring now to FIG. 1, a largely exploded view of the blood-glucose meter integrated with a biological test-piece tank in accordance with the present invention is shown. The blood-glucose meter integrated with a biological test-piece tank includes mainly a biological test-piece tank 1 and a blood-glucose meter 2. The biological test-piece tank 1 includes internally a chamber 11 for providing an accommodation room to store a plurality of biological test pieces. The biological test-piece tank 1 is furnished with a tank opening 12 at a top thereof. The tank opening 12 pairs a cover 14 so as to form a sealed structure. Opposing to the top as well as the cover 14 of the biological test-piece tank 1, a tank bottom 13 thereof is included. The blood-glucose meter 2, connected with the tank bottom 13, has an inserting hole 22 for receiving a biological test piece 3. The biological test piece 3 can carry thereon a biological specimen to be examined for obtaining a corresponding blood-glucose value.

The blood-glucose meter 2 further includes a display unit 21 for displaying the blood-glucose value of the specimen. In the present invention, the display unit 21 can be an LCD. In addition, the blood-glucose meter 2 is further furnished with a setup button 23 for setting up related parameters.

Figure 2:
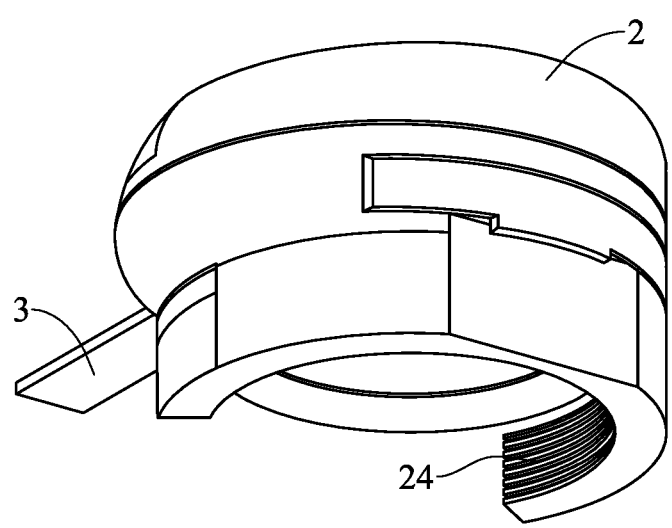
FIG. 2 is a schematically perspective view of a first embodiment of the blood-glucose meter to be engaged with the biological test-piece tank in accordance with the present invention.
Figure 3:
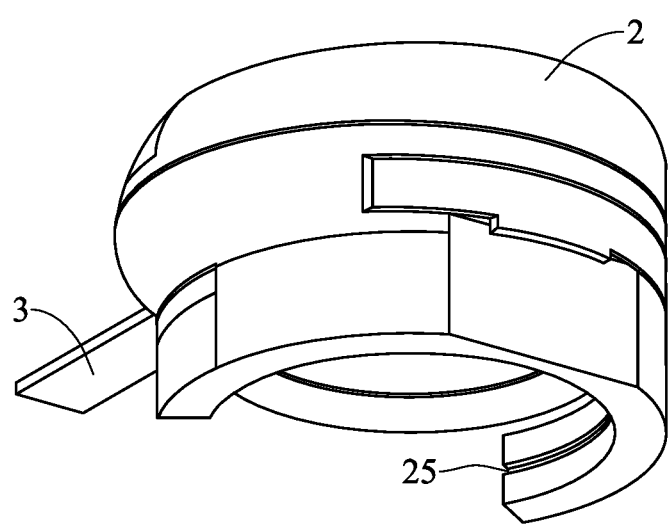
FIG. 3 is a schematically perspective view of a second embodiment of the blood-glucose meter to be engaged with the biological test-piece tank in accordance with the present invention.
Figure 4:
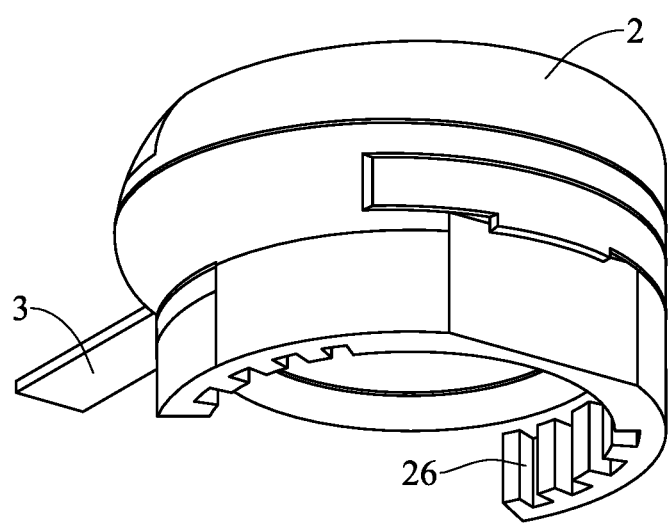
FIG. 4 is a schematically perspective view of a third embodiment of the blood-glucose meter to be engaged with the biological test-piece tank in accordance with the present invention.

Referring now to FIG. 2, FIG. 3 and FIG. 4, three embodiments of the blood-glucose meter 2 to engage the biological test-piece tank 1 are shown perspectively to present individual engagement means for integrating the blood-glucose meter 2 and the biological test-piece tank 1. In FIG. 2, the engagement means is a screw pair to perform an engagement in a screwing manner between the blood-glucose meter 2 and the biological test-piece tank 1. Such a screw pair is embodied by constructing external threads (not shown in the figure) exteriorly at the tank opening 12 and corresponding internal threads 24 interiorly at the blood-glucose meter 2. In FIG. 3, the engagement means is a notch pair to perform an engagement in a notching manner between the blood-glucose meter 2 and the biological test-piece tank 1. Such a notch pair is embodied by constructing a bulge ring (not shown in the figure) exteriorly at the tank opening 12 and a corresponding internal groove 25 interiorly at the blood-glucose meter 2. In FIG. 4, the engagement means includes a C-shape tooth ring located in an engagement area of the blood-glucose meter 2 and the biological test-piece tank 1. In this embodiment, the C-shape tooth ring is constructed as a C-shape internal-tooth ring 26 interiorly at the blood-glucose meter 2. The existence of the C-shape internal-tooth ring 26 can increase substantially the friction between the blood-glucose meter 2 and the biological test-piece tank 1, such that a goal of firm engagement can thus be achieved. However, in another embodiment not shown here, the C-shape tooth ring can be constructed as a C-shape external-tooth ring exteriorly at the tank opening 12. In addition, in a further embodiment not shown here, the engagement means can be a mesh pair to perform an engagement in a tooth-meshing manner between the blood-glucose meter 2 and the biological test-piece tank 1. Such a mesh pair is embodied by constructing a C-shape external-tooth ring exteriorly at the tank opening 12 and a corresponding C-shape internal-tooth ring interiorly at the blood-glucose meter 2.

By introducing the blood-glucose meter integrated with a biological test-piece tank as depicted from FIG. 1 to FIG. 4, following advantages are obvious.

(1) In the present invention, a small-sized blood-glucose meter and a biological test-piece tank are integrated as a unique apparatus, so that the blood-glucose meter can serve as a cover of the biological test-piece tank to ensure dryness of the biological test pieces. More importantly, by integrating the blood-glucose meter and the biological test-piece tank, no bothering situation of "finding the biological test-piece tank but not the blood-glucose meter" or "finding the blood-glucose meter but not the biological test-piece tank" can happen anymore. Thereupon, a better arrangement in storing and preserving the blood-glucose meter and the biological test-piece tank can be achieved.

(2) In the present invention, after the blood-glucose meter is integrated with the biological test-piece tank, the total volume is reduced, and thus easiness in storage and preservation can be obtained.

(3) In the present invention, while in usage, the blood-glucose meter can work with or without the biological test-piece tank integrated. Thus, according to practical needs, a user can decide if the blood-glucose meter is to be applied along with the biological test-piece tank, and thereupon the usage convenience thereof can be substantially enhanced.

In summary, the blood-glucose meter integrated with a biological test-piece tank provided by the present invention is also featured in less components, easy manufacturing and lower cost. Therefore, the blood-glucose meter integrated with a biological test-piece tank provided by the present invention is already sufficient to satisfy the demand of the art, and also able to promote the competitive of this industry.

By viewing the aforesaid advantages, it is proved that, in the art of biological testing instruments, the blood-glucose meter integrated with a biological test-piece tank can achieve great commercial profits, and thus is worth of persuading a patent protection.

While the present invention has been particularly shown and described with reference to a preferred embodiment, it will be understood by those skilled in the art that various changes in form and detail may be without departing from the spirit and scope of the present invention.

What is claimed is:

1. A blood-glucose meter integrated with a biological test-piece tank, comprising:

a biological test-piece tank comprising:
   a first top surface;
   a first bottom surface;
   a hollow cylindrical body connecting the first top surface and the first bottom surface, wherein the hollow cylindrical body forms an internal chamber for storing a plurality of biological test pieces; and
   the biological test-piece tank further comprising a first opening at the first top surface and a second opening at the first bottom surface; and
a removable cover configured to form a sealed fit with the second opening at the first bottom surface of the biological test-piece tank; and
a blood-glucose meter comprising;
   a second top surface;
   a second bottom surface;
   a hole configured to receive a one of the plurality of biological test pieces;
   wherein the blood-glucose meter further comprises a downwardly protruding semi-circular ring extending from the second bottom surface, the downwardly protruding semi-circular ring configured to form a sealed connection with the first opening at the first top surface of the biological test-piece tank,
   wherein the downwardly protruding semi-circular ring further comprises a plurality of radially inwardly protruding teeth configured to frictionally engage the first top surface and hollow cylindrical body of the biological test-piece tank; and
   wherein the one of the plurality of biological test pieces carrying thereon a biological specimen configured to be examined by the blood-glucose meter.

2. The blood-glucose meter integrated with a biological test-piece tank of claim 1, wherein the blood-glucose, meter further includes a display unit configured to display a blood glucose value.

3. The blood glucose meter integrated with a biological test-piece tank of claim 2, wherein the display unit is an LCD.

4. The blood-glucose meter integrated with a biological test-piece tank of claim 1, wherein the blood-glucose meter further includes a setup button configured to set parameters.

* * * * *